(12) United States Patent
Shimizu et al.

(10) Patent No.: US 6,596,364 B2
(45) Date of Patent: Jul. 22, 2003

(54) SQUARYLIUM COMPOUNDS AND OPTICAL RECORDING MEDIUM CONTAINING THE SAME

(75) Inventors: Ikuo Shimizu, Yokkaichi (JP); Hiroshi Toyoda, Yokkaichi (JP); Motoharu Kinugasa, Yokkaichi (JP); Shiho Yamada, Yokkaichi (JP); Masanori Ikuta, Yokkaichi (JP); Kenji Mutoh, Tokyo (JP); Tsutomu Satoh, Tokyo (JP); Tatsuya Tomura, Tokyo (JP)

(73) Assignees: Kyowa Hakko Kogyo Co., Ltd., Tokyo (JP); Kyowa Yuka Co., Ltd., Tokyo (JP); Ricoh Company, Ltd., Tokyo (JP)

( * ) Notice: Subject to any disclaimer, the term of this patent is extended or adjusted under 35 U.S.C. 154(b) by 0 days.

(21) Appl. No.: 09/913,505

(22) PCT Filed: Dec. 15, 2000

(86) PCT No.: PCT/JP00/08891

§ 371 (c)(1),
(2), (4) Date: Dec. 5, 2001

(87) PCT Pub. No.: WO01/44233

PCT Pub. Date: Jun. 21, 2001

(65) Prior Publication Data

US 2003/0082330 A1 May 1, 2003

(30) Foreign Application Priority Data

Dec. 16, 1999 (JP) .......................................... 11-357361

(51) Int. Cl.$^7$ ................................................. B32B 3/02
(52) U.S. Cl. ................ 428/64.1; 428/64.8; 430/270.14
(58) Field of Search .............................. 428/64.1, 64.4, 428/64.8, 913; 430/270.14, 495.1, 945

(56) References Cited

U.S. PATENT DOCUMENTS 5,510,229 A * 4/1996 Satoh ..................... 430/270.18
5,681,685 A * 10/1997 Yamaoka ................. 430/281.1

FOREIGN PATENT DOCUMENTS

| DE | 2 055 894 | 5/1972 |
| EP | 0 568 877 | 11/1993 |
| JP | 5-339233 | 12/1993 |
| JP | 6-263732 | 9/1994 |

\* cited by examiner

*Primary Examiner*—Elizabeth Mulvaney
(74) *Attorney, Agent, or Firm*—Finnegan, Henderson, Farabow, Garrett & Dunner, L.L.P.

(57) ABSTRACT

Squarylium compounds having spectroscopic properties, light resistance, solubility and thermal decomposition properties suitable for a recording material for DVD-R represented by the general formula (I), having pyrazole and indoline skeletons in the molecule and optical recording media having a recording layer comprising an asymmetric squarylium compound of formula (I).

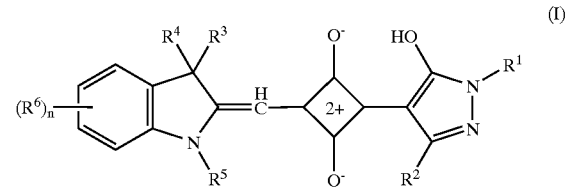

11 Claims, 1 Drawing Sheet

Fig. 1

SQUARYLIUM COMPOUNDS AND OPTICAL RECORDING MEDIUM CONTAINING THE SAME

TECHNICAL FIELD

The present invention relates to novel squarylium compounds which can be used in the optical recording field, and to optical recording media using the same.

BACKGROUND ART

In recent years, development of a digital versatile disc-recordable (DVD-R) as a recordable optical recording medium having a higher recording density than that of a compact disc-recordable (CD-R) has been under. Both of CD-R and DVD-R are similar to each other in that an organic dye is utilized therein as a recording material and in a principle of recording and reproducing of a signal (information). Therefore, the organic dyes developed for CD-R can basically comply with the various requirements (light resistance, solubility, thermal decomposition properties) for the recording material of DVD-R other than spectroscopic properties. However, an oscillation wavelength of a semiconductor laser, which is used for recording the signal to DVD-R or for reproducing the signal from DVD-R, is in the range of 600–700 nm, which is shorter than that of the semiconductor laser which is used for CD-R. Accordingly, the recording material utilized for DVD-R should have an absorbance end of a longer wavelength side shorter than that of CD-R when it exists in the form of a membrane. Therefore, the dyes developed for CD-R such as cyanine dyes, azaannulene dyes and indoaniline-metal chelate dyes ("Electronics Related Dyes", CMC, 1998) can not be used as the recording material for DVD-R.

The present inventors have developed squarylium compounds having different two kinds of aromatic substituents in a molecule. Such squarylium compounds have a squaric acid skeleton at a center of the molecule and substituents comprising an aromatic compound on carbon atoms at two catercornered positions of the skeleton. Squarylium compounds having two same aromatic substituents are conveniently referred to as symmetric squarylium compounds (or symmetric squarylium dyes), whereas those having different two kinds of substituents are referred to as asymmetric squarylium compounds (or asymmetric squarylium dyes).

The symmetric squarylium compounds having the same two pyrazole structures in the molecule have been already known (DE 2055894). In addition, some kinds of asymmetric squarylium compounds having one indoline structure and another aromatic substituent different from the indoline structure in the molecule have been known (Japanese Unexamined Patent Publication No. 339233/1993). However, asymmetric squarylium compounds having only one pyrazole structure, or having one pyrazole and one indoline structures have not been known yet.

In view of an oscillation wavelength of the semiconductor laser used for DVD-R, for spectroscopic properties of the recording material, which have the close relation with recording and reproducing sensitivities of the signal, it is desirable that the maximum absorption wavelength ($\lambda_{max}$) of the recording material measured in its liquid state is within the range of 550–600 nm and log $\epsilon$ thereat ($\epsilon$ is a molar extinction coefficient) is 5 or greater. In addition, for thermal decomposition properties of the recording material, which have the close relation with the recording sensitivity, it is desirable that a significant loss in weight is observed within the temperature range of 250–350° C.

Furthermore, although light resistance and solubility in a solvent which is necessary for membrane formation are also required as the property of the recording material, there is no recording material having suitable properties for DVD-R, such as spectroscopic properties, light resistance, solubility and thermal decomposition properties, in the known squarylium compounds.

DISCLOSURE OF THE INVENTION

An object of the present invention is to provide squarylium compounds having spectroscopic properties, light resistance, solubility and thermal decomposition properties suitable as a recording material for DVD-R, and optical recording media using the same.

In view of the above situation, the present inventors intensively investigated and, as the result, we successfully synthesized novel asymmetric squarylium compounds having pyrazole and indoline skeletons in the molecule, and obtained a finding that such squarylium compounds have properties suitable as a recording material for DVD-R.

The present invention was done based on such a finding, and provides squarylium compounds represented by the formula (I):

wherein, $R^1$ represents a hydrogen atom, an alkyl group optionally having a substituent, an aryl group optionally having a substituent, or a heterocyclic group optionally having a substituent; $R^2$ represents a hydrogen atom, a halogen atom, an alkyl group optionally having a substituent, an alkoxy group optionally having a substituent, an aralkyl group optionally having a substituent, an aryl group optionally having a substituent, an amino group optionally having a substituent or a heterocyclic group optionally having a substituent; $R^3$ and $R^4$ are the same or different, and represent an alkyl group, or $R^3$ and $R^4$ may be taken together with an adjacent carbon atom to form an alicyclic hydrocarbon ring or a heterocycle; $R^5$ represents a hydrogen atom, an alkyl group optionally having a substituent, an aralkyl group optionally having a substituent or an aryl group optionally having a substituent; $R^6$ represents a halogen atom, an alkyl group optionally having a substituent, or an aralkyl group, an aryl group, a nitro group, a cyano group or an alkoxy group; and n represents an integer of 0–4, and when n is 2–4, then $R^6$s are the same or different, or two adjacent $R^6$s may be taken together with two adjacent carbon atoms to form an aromatic ring optionally having a substituent, and optical recording media which has a recording layer comprising said squarylium compound.

BRIEF DESCRIPTION OF THE DRAWINGS

Description of Drawing

Description of Symbols

T1: Weight losing-initiation temperature.

T2: Weight losing-termination temperature.

M0: Initial weight,
m1: Ratio of remaining weight at T1, and
m2: Ratio of remaining weight at T2.

BEST MODE FOR CARRYING OUT THE INVENTION

Detailed Description of the Invention

The present invention will be illustrated below, and herein the compound represented by the formula (I) is referred to as a compound (I). This is also applicable to compounds with other formula numbers added.

First, in the definition of substituents in the above formula (I), an alkyl part of the alkyl and alkoxy groups includes straight or branched alkyl groups having from 1 to 6 carbon atoms and cyclic alkyl groups having from 3 to 8 carbon atoms, such as methyl, ethyl, propyl, iso-propyl, butyl, iso-butyl, sec-butyl, tert-butyl, pentyl, iso-pentyl, 1-methylbutyl, 2-methylbutyl, tert-pentyl, hexyl, cyclopropyl, cyclobutyl, cyclopentyl, cyclohexyl, cycloheptyl and cyclooctyl groups, and the like.

Examples of the aralkyl group include aralkyl groups having from 7 to 15 carbon atoms, such as benzyl, phenethyl, phenylpropyl and naphthylmethyl groups, and the like.

Examples of the aryl group include phenyl, naphthyl and anthryl groups, and the like.

The halogen atom includes chlorine, bromine, fluorine and iodine atoms.

The substituents for the aralkyl group, the aryl group, the alkoxy group, the aromatic ring or the heterocyclic group are the same or different 1 to 5 subtutituents, and include, for example, a hydroxyl group, a carboxyl group, a halogen atom, an alkyl group, an alkoxy group and a nitro group, and the like, wherein the halogen atom, the alkyl group and the alkoxy group include those as described above.

The substituents for the alkyl group are the same or different 1 to 3 substituents, and include, for example, a hydroxyl group, a carboxyl group, a halogen atom, an alkoxy group, and the like, wherein the halogen atom and the alkoxy group include those as described above.

The substituents for the amino group are the same or different 1 or 2 alkyl groups, wherein the alkyl group includes those as described above.

The aromatic ring which is formed by two adjacent $R^6$s being taken together with two adjacent carbon atoms includes a benzene ring, and the like.

The heterocyclic group in the heterocyclic group or the heterocycle which is formed by $R^3$ and $R^4$ being taken together with two adjacent carbon atoms includes aromatic heterocycles and alicyclic heterocycles.

Examples of the aromatic heterocycle include 5- or 6-membered monocyclic aromatic heterocycles containing at least one atom selected from nitrogen, oxygen and sulfur atoms, fused di- or tri-cyclic aromatic heterocycles, which are formed by fusing 3- to 8-membered rings and which contain at least one atom selected from nitrogen, oxygen and sulfur atoms, and the like, and, more particularly, include pyridine, pyrazine, pyrimidine, pyridazine, quinoline, isoquinoline, phthalazine, quinazoline, quinoxaline, naphthyridine, cinnoline, pyrrole, pyrazole, imidazole, triazole, tetrazole, thiophene, furan, thiazole, oxazole, indole, isoindole, indazole, benzimidazole, benzotriazole, benzothiazole, benzoxazole, purine and carbazole rings, and the like.

In addition, examples of the alicyclic heterocycle include 5- or 6-membered mono-alicyclic heterocycles containing at least one atom selected from nitrogen, oxygen and sulfur atoms, fused di- or tri-alicyclic heterocycles, which are formed by fusing 3- to 8-membered rings and which contain at least one atom selected from nitrogen, oxygen and sulfur atoms, and the like, and, more particularly, include pyrrolidine, piperidine, piperazine, morpholine, thiomorpholine, homopiperidine, homopiperazine, tetrahydropyridine, tetrahydroquinoline, tetrahydroisoquinoline, tetrahydrofuran, tetrahydropyran, dihydrobenzofuran and tetrahydrocarbazole rings, and the like.

Examples of the alicyclic hydrocarbon ring which is formed by $R^3$ and $R^4$ being taken together with an adjacent carbon atom include saturated or unsaturated alicyclic hydrocarbons having from 3 to 8 carbon atoms, such as cyclopropane, cyclobutane, cyclopentane, cyclohexane, cycloheptane, cyclooctane, cyclopentene, 1,3-cyclopentadiene, cyclohexene and cyclohexadiene rings, and the like.

A general method for preparing the compound (I) will be illustrated below.

Scheme (1-a)

Scheme (1-a)

The compound (IV) is prepared by reacting the compound (II) with 1- to 2- fold mole of the compound (IIIa) or (IIIb) in a solvent, if needed, in the presence of 1- to 2-fold mole of a base, at 0° C. to room temperature for 30 minutes to 70 hours.

Examples of the solvent include halogenated hydrocarbons such as chloroform, dichloromethane, 1,2-dichloroethane, and the like; ethers such as diethyl ether, t-butyl methyl ether, and the like; aromatic hydrocarbons such as toluene, benzene, and the like; alcohols such as methanol, ethanol, propanol, and the like; tetrahydrofuran, ethyl acetate, dimethylformamide, dimethyl sulfoxide, and the like.

Scheme (1-b)

The compound (V) is prepared by reacting the compound (IV) in a 50–90 volume/volume % aqueous solution of acetic acid at 90–110° C. for 1–7 hours, or in 50–99% by weight of an aqueous solution of trifluoroacetic acid at 45–50° C. for 1–3 hours.

Examples of the base include organic bases such as quinoline, triethylamine, pyridine, and the like, and inorganic bases such as potassium carbonate, potassium hydrogen carbonate, sodium hydrogen carbonate, and the like.

Scheme (1-c)

The compound (I) is prepared by reacting the compound (V) with 0.5- to 2-fold mole of the compound (VI) in a solvent, if needed, in the presence of 0.5- to 2-fold mole of a base, at 80–120° C. for 1–15 hours.

Examples of the solvent to be used include only alcoholic solvents having from 2 to 8 carbon atoms such as ethanol, propanol, iso-propanol, butanol, octanol, and the like, and a mixture of the alcoholic solvent and benzene or toluene (50 volume/volume % or more of alcohol is contained).

Examples of the base to be used include organic bases such as quinoline, triethylamine, pyridine, and the like, and inorganic bases such as potassium carbonate, potassium hydrogen carbonate, sodium hydrogen carbonate, and the like.

Scheme(2-a)

The compound (VII) is prepared by reacting the compound (II) with 1- to 2-fold mole of the compound (VI) in a solvent in the presence of 1- to 2-fold mole of a base at 0–40° C. for 1–20 hours, followed by collecting the resulting precipitate by filtration and treating it with an acidic aqueous solution.

Examples of the solvent include those as described for the Scheme (1-a).

Examples of the base to be used include organic bases such as quinoline, triethylamine, pyridine, and the like, and inorganic bases such as potassium carbonate, potassium hydrogen carbonate, sodium carbonate, sodium hydrogen carbonate, potassium hydroxide, sodium hydroxide, and the like.

Examples of the acidic aqueous solution include an aqueous solution of hydrochloric acid, or the like.

Scheme (2-b)

The compound (VIII) is prepared by conducting a procedure similar to that described for the Scheme (1-b) but using the compound (VII) instead of the compound (IV), or by reacting the compound (VII) in a 3–100 volume/volume % mixture of an acidic aqueous solution and an organic solvent at room temperature to 100° C. for 1–10 hours.

Scheme (2-c)

wherein $R^1$, $R^2$, $R^3$, $R^4$, $R^5$, $R^6$ and n have the same meanings as defined above, X represents a halogen atom such as chlorine, bromine or iodide, a tosyl or mesyl group, or the like, and Y represents a halogen atom such as chlorine or bromine, or $OR^7$ ($R^7$ represents an alkyl group), wherein the alkyl group has the same meaning as defined above.

Examples of the organic solvent include dimethylformamide, dimethyl sulfoxide, tetrahydrofuran, 1,4-dioxane, and the like.

Examples of the acidic aqueous solution include an aqueous solution of hydrochloric acid, trifluoroacetic acid, or the like.

or filtration, and if needed, by further purification with procedures conventionally utilized in the synthetic organic chemistry (column chromatography, recrystallization, washing with a solvent, or the like).

Embodiments of the compound (I) are shown in Table 1.

TABLE 1

Embodiments of squarylium compound (I)

| Compounds | $R^1$ | $R^2$ | $R^3$ | $R^4$ | $R^5$ | n | $R^6$ |
|---|---|---|---|---|---|---|---|
| 1 | Ph | Me | Me | Me | Me | 0 | — |
| 2 | Ph | Me | Me | Me | Me | 1 | 2-OMe |
| 3 | Ph | Me | Me | Me | Me | 1 | 2-Cl |
| 4 |  | Me | Me | Me | Me | 0 | — |
| 5 |  | Me | Me | Me | Me | 0 | — |
| 6 |  | Me | Me | Me | Me | 0 | — |
| 7 |  (4-NO$_2$-Ph) | pyrrolidinyl | Me | Me | Me | 0 | — |
| 8 | Ph | Me | Me | Me | Me | 2 | 1-A-2 |
| 9 | Ph | Me | Me | Me | Et | 2 | 1-A-2 |
| 10 | Me | Me | Me | Me | nBu | 0 | — |
| 11 | Ph | CF$_3$ | Me | Me | Me | 0 | — |
| 12 | H | nPr | Me | Me | Me | 0 | — |
| 13 | Ph | iPr | Me | Me | Me | 0 | — |
| 14 | Me | Me | —(CH$_2$)$_5$— | Me | 0 | — |
| 15 | tBu | Me | Me | Me | Me | 1 | 2-Cl |
| 16 | H | Ph | Me | Me | Me | 0 | — |
| 17 | Me | nPr | Me | Me | Me | 1 | 2-Me |

Me: methyl,
Et: ethyl,
nPr: propyl,
iPr: iso-propyl,
nBu: butyl,
tBu: tert-butyl, and
Ph: phenyl Scheme (2-c)

The compound (I) can be prepared by conducting a procedure similar to that described for the Scheme (1-c) but using the compound (VIII) instead of the compound (V), and using the compound (IIIa) or compound (IIIb) instead of the compound (VI).

After the reaction, the compound (I) is purified and isolated, for example, by conducting distillation of a solvent wherein A represents —CH═CH—CH═CH—.

Next, the constitution of a recording medium utilizing the squarylium compound of the present invention (hereinafter, it may be referred to as "a compound of the present invention") will be illustrated.

The physical properties required for a material for a recording layer include optical and thermal properties. The optical properties are preferably such that there is a large absorption band at a shorter wavelength side than 600–700 nm, preferably 630–690 nm, which is a recording or reproducing wavelength of DVD-R or the like, and a recording or reproducing wavelength is in the vicinity of a longer wavelength end of the above-mentioned absorption band. This means that the above-mentioned material for the recording layer has a greater refractive index and extinction coefficient within 600–700 nm, which is a recording or reproducing wavelength.

More particularly, the refractive index "n" of a single layer of the recording layer is preferably 1.5–3.0, and the extinction coefficient "k" of a single layer of the recording layer is preferably within the range of 0.02–0.3, at the wavelength range of the recording or reproducing wavelength ±5 nm in the vicinity of the longer wavelength end of the above-mentioned absorption band. When "n" is 1.5 or greater, a modulation depth of recording becomes higher, and when "n" is 3.0 or smaller, an error does not occur with the light in the recording or reproducing wavelength range. In addition, when "k" is 0.02 or greater, the recording sensitivity is improved, and when "k" is 0.3 or smaller, the reflectance of 50% or greater can be easily obtained.

In addition, the maximum absorption wavelength ($\lambda_{max}$) of the material for the recording layer which is measured in its liquid state is preferably within the range of 550–600 nm, and loge thereat ($\epsilon$ is a molar extinction coefficient) is preferably 5 or bigger.

In order to evaluate the thermal properties of the aforementioned squarylium compound, thermogravimetric analysis was performed to observe the loss in weight due to temperature rising. Herein, among some weight in loss processes (loss process), one having the greatest degree of the loss in weight is referred to as a principal loss-in-weight process.

For the thermal properties, it is necessary that the loss in weight in the principal loss-in-weight process is steep relative to a temperature change, because the compound of the present invention is decomposed in the principal loss-in-weight process, and causes a decrease in a membrane thickness and a change in optical constants and, thereby, a recording portion in an optical sense is formed. Accordingly, when the loss in weight in the principal loss-in-weight process is shelvy relative to the temperature change, it becomes extremely disadvantageous to form a high density recording portion because the recording portion is formed over a wide temperature range. For the similar reason, the material having multiple loss-in-weight processes is also disadvantageous in application to the high recording density.

In the present invention, the temperature slope of the loss in weight is calculated as follows.

Figure 1:
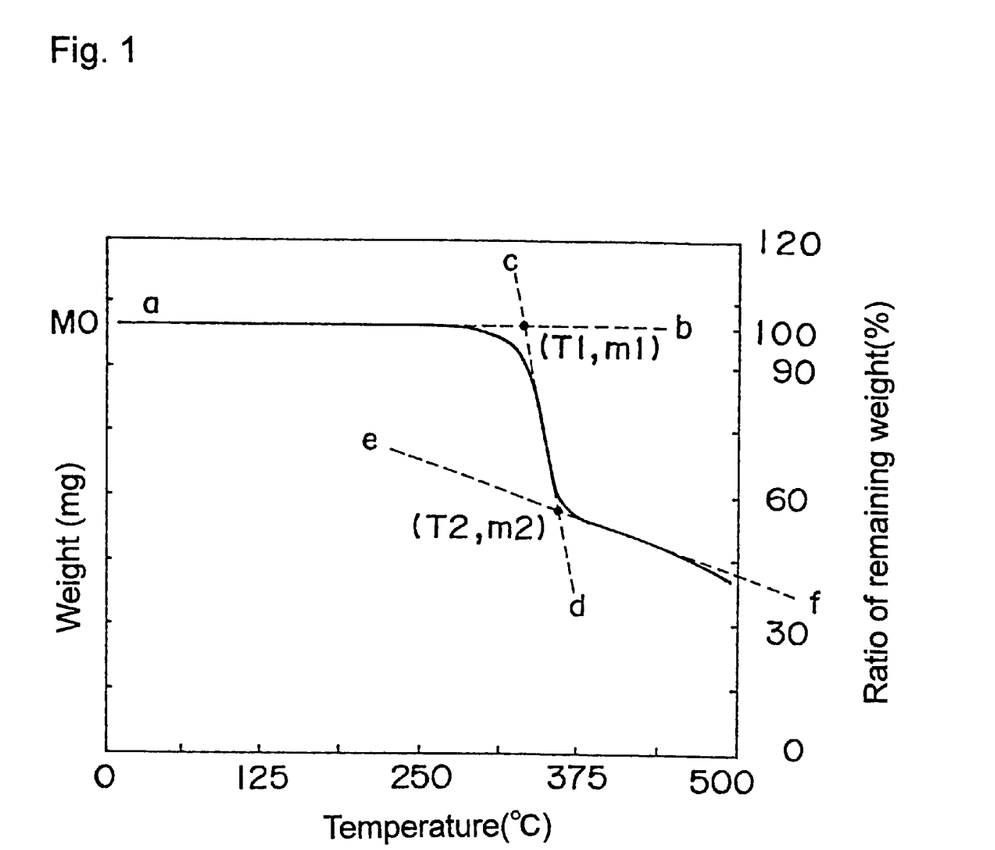
FIG. 1 is a graph illustrating a typical thermogravimetric curve (heating speed of 10° C./min.) for the squarylium compound of the present invention.

As illustrated in FIG. 1, a temperature of the compound of the present invention of the weight M0 is risen at a rate of 10° C./min. under the nitrogen atmosphere. As the temperature rises, the weight of the compound slightly decreases almost along the straight line a-b, and the weight steeply decreases almost along the straight line c-d after reaching the certain temperature. As the temperature further rises, a steep loss in weight is terminated and the loss in weight almost along the straight line e-f is caused. In the graph, at an intersection point of the straight lines a-b and c-d, a temperature is defined as T1 (° C.), and a ratio of the remaining weight relative to the initial weight M0 is defined as m1 (%). In addition, at an intersection point of the straight lines c-d and e-f, a temperature is defined as T2 (° C.), and a ratio of the remaining weight relative to the initial weight M0 is defined as m2 (%).

That is, in the principal loss-in-weight process, a weight losing-initiation temperature is t1, a weight losing-termination temperature is T2, and a ratio of the loss in weight is represented by:

$$(m1-m2)(\%), \text{ and}$$

a temperature slope of the loss in weight is represented by:

$$(m1-m2)(\%)/(T2-T1)(° C.).$$

According to the above definitions, a recording material utilized for the optical information recording medium has preferably the temperature slope of the loss in weight in the principal loss-in-weight process of 1%/° C. or greater. When the recording material having the temperature slope of the loss in weight of 1%/° C. or greater is used, a groove width of the recording portion is not widen, and a shorter recording portion can be easily formed.

In addition, the ratio of the loss in weight in the principal loss-in-weight process for the recording material is preferably 20% or greater. When the ratio of the loss in weight is 20% or greater, it allows a better modulation depth of recording and recording sensitivity.

Moreover, for the thermal properties, it is necessary that the weight losing-initiation temperature (T1) is within the particular temperature range. More particularly, the weight losing-initiation temperature is preferably 350° C. or lower, and more preferably within the range of 250–350° C. When the weight losing-initiation temperature is 350° C. or lower, it is not necessary to raise the power of the recording laser beam, and when it is 250° C. or higher, it is preferable in a recording stability sense.

The preferable substrate shape is under the condition that a track pitch is within the range of 0.7–0.8 μm and a groove width at the half band width is within the range of 0.20–0.36 μm.

The substrate usually has a guiding groove having a depth of 1,000–2,500 Å. The track pitch is usually 0.7–1.0 μm, but is preferably 0.7–0.8 μm for the high recording density application. The groove width is preferably 0.18–0.36 μm as the half band width. When the groove width is 0.18 μm or wider, the adequate strength of a tracking error signal can be easily detected, whereas when it is 0.36 μm or narrower, the recording portion is hardly widened in a traverse direction upon recording, being preferable.

1. The Structure of an Optical Recording Medium

The optical recording medium of the present invention may be formed into an air-sandwich structure or into a closely adhered structure which is applied to general recordable discs, or may be formed into a structure of a recordable optical recording medium such as CD-R, DVD-R, or the like.

2. The Required Properties and Embodiments of Constituent Materials for Each Layer The optical recording medium of the present invention has a basic structure in which a first substrate and a second substrate are adhered via a recording layer with an adhesive. The recording layer may be a single layer of an organic dye layer comprising the compound of the present invention, or may be a laminated layer of the organic dye layer and a metal refractive layer for enhancing the reflectance. Between the recording layer and the substrate, an undercoat layer or a protective layer may be built-up, or they may be laminated for improving the function. Most frequently used structure is the first substrate/the organic dye layer/the metal refractive layer/the protective layer/the adhesive layer/the second substrate.

a. Substrate

The substrate to be used should be transmittable to the wavelength of the laser beam to be used when recording or reproducing is conducted from a substrate side, but it is not necessary for the substrate to be transmittable to the wavelength when recording or reproducing is conducted from a recording layer side. As the material for the substrate, for example, plastics such as polyester, acrylic resin, polyanride, polycarbonate resin, polyolefin resin, phenolic resin, epoxy resin, polyimide, or the like, glasses, ceramics, metals or the like may be used. Furthermore, a guiding groove or a guiding pit for tracking, a preformat such as an addressing signal, or the like may be formed on a surface of the substrate.

b. Recording Layer

The recording layer is a layer in which some optical change is caused by irradiation with a laser beam and, thereby, an information is recorded, and should contain the compound of the present invention. The compounds of the present invention may be used alone or in combination of two or more for forming the recording layer.

In addition, the compound of the present invention may be used by mixing it or laminating it with other organic dyes, metals dr metal compounds for the purpose of enhancement of the optical properties, the recording sensitivity, the signal properties, or the like. Examples of the organic dye include a polymethine dye, naphthalocyanine, phthalocyanine, squarylium, croconium, pyrylium, naphthoquinone, anthraquinone (indanthrene), xanthene, triphenylmethane, azulene, tetrahydrocholine, phenanthrene and triphenothiazine dyes, metal complex compounds, and the like. Examples of the metal and metal compound include In, Te, Bi, Se, Sb, Ge, Sn, Al, Be, $TeO_2$, SnO, As, Cd, and the like, each of which may be used in the form of dispersion mixture or lamination.

In addition, it is possible to enhance the light resistance significantly by mixing a light stabilizer into the compound of the present invention. As the light stabilizer, metal complexes and aromatic amines are preferable. Embodiments of the light stabilizer will be listed below (see Tables 2 and 3).

The mixing ratio of the light stabilizer relative to the compound of the present invention is preferably 5–40% by weight. When the ratio is less than 5% by weight, the effect is low, whereas when the ratio is above 40% by weight, the recording or reproducing properties may be adversely effected in some cases.

In addition, macromolecular materials, for example, various materials such as ionomer resin, polyamide resin, vinyl resin, natural polymer, silicone or liquid rubber, or silane coupling agents may be dispersed and mixed into the compound of the present invention, and additives such as stabilizers (for example, transition metal complex), dispersing agents, flame retardants, lubricants, antistatic agents, surfactants or plasticizers may be used together for the purpose of modifying the properties.

The recording layer may be formed using conventional methods such as a deposition, a sputtering, a chemical vapor deposition or a solvent coating. In the case where the coating method is used, the dye comprising the compound of the present invention optionally with the aforementioned additives added is dissolved in an organic solvent, and the solution is coated by the conventional coating method such as a spraying, a roller coating, a dipping or a spin coating.

Examples of the organic solvent to be used generally include alcohols such as methanol, ethanol and iso-propanol, ketones such as acetone, methyl ethyl ketone and cyclohexanone, amides such as N,N-dimethylformamide and N,N-dimethylacetoamide, sulfoxides such as dimethyl sulfoxide, ethers such as tetrahydrofuran, dioxane, diethyl ether and ethyleneglycol monomethyl ether, esters such as methyl acetate and ethyl acetate, aliphatic halogenated hydrocarbons such as chloroform, methylene chloride, dichloroethane, carbon tetrachloride and trichloroethane, aromatic compounds such as benzene, xylene, monochlorobenzene and dichlorobenzene, cellosolves such as methoxyethanol and ethoxyethanol, and hydrocarbons such as hexane, pentane, cyclohexane and methylcyclohexane.

The membrane thickness of the recording layer is preferably 100 Å–10 μm, more preferably 200–2000 Å.

Embodiments of the light stabilizer to be used in combination with the compound of the present invention are shown below.

(1) Metal complex-light stabilizers (see Table 2)

(A)

wherein $R_a$ and $R_b$ are the same or different, and represent a hydrogen atom, an alkyl group optionally having a substituent, an aryl group or a heterocyclic group.

(B)

wherein $R_a$, $R_b$, $R_c$ and $R_d$ are the same or different, and represent a hydrogen atom, a halogen atom, an alkyl group bonding directly or indirectly via a divalent linking group, an aryl group, a cyclic alkyl group or a heterocyclic group.

(C)

wherein X represents O, S or $CR_aR_b$, wherein $R_a$ and $R_b$ are the same or different, and represent CN, $COR_c$, $COOR_d$, $CONR_eR_f$, $SO_2R_g$, or a group of atoms necessary for forming a 5- or 6-membered ring, and wherein $R_c$–$R_g$ are the same or different, and represent an alkyl group optionally having a substituent or an aryl group.

(D)

wherein $R_a$, $R_b$, $R_c$ and $R_d$ are the same or different, and represent a hydrogen atom, a halogen atom, an alkyl group bonding directly or indirectly via a divalent linking group, an aryl group, a cyclic alkyl group or a heterocyclic group, and Rd represents a hydrogen atom, an alkyl group, an aryl group, an acyl group, a carboxyl group, an alkoxycarbonylalkyl group or a sulfo group.

(E)

wherein $R_a$, $R_b$, $R_c$ and $R_d$ are the same or different, and represent a hydrogen atom, a halogen atom, an alkyl group bonding directly or indirectly via a divalent linking group, an aryl group, a cyclic alkyl group or a heterocyclic group, and $R_e$ and $R_f$ are the same or different, and represent a hydrogen atom, an alkyl group, an aryl group, an acyl group, a carboxyl group or a sulfo group.

(F)

wherein X represents O or S, $R_a$, $R_b$ and $R_c$ are the same or different, and represent an alkyl group optionally having a substituent bonding directly or via an oxy group, a thio group or an amino group, an aryl group or a cyclic alkyl group, and the symbol:═══
represents C═C—C or C—C═C.

(G)

wherein X represents O or S, $R_a$, $R_b$ and $R_c$ are the same or different, and represent an alkyl group optionally having a substituent bonding directly or via an oxy group, a thio group or an amino group, an aryl group or a cyclic alkyl group, $R_d$ represents an alkyl group or an aryl group, and the symbol:═══
represents C═C—C or C—C═C.

(H)

wherein $R_a$ and $R_b$ are the same or different, and represent a hydrogen atom, an alkyl group optionally having a substituent, an aryl group or a heterocyclic group.

(I)

wherein $R_a$, $R_b$, $R_c$ and $R_d$ are the same or different, and represent a hydrogen atom, a halogen atom, an alkyl group bonding directly or indirectly via a divalent linking group, an aryl group, a cyclic alkyl group or a heterocyclic group.

(J)

wherein $R_a$, $R_b$, $R_c$ and $R_d$ are the same or different, and represent a hydrogen atom, a halogen atom, an alkyl group bonding directly or indirectly via a divalent linking group, an aryl group, a cyclic alkyl group or a heterocyclic group, $R_e$ represents a hydrogen atom, an alkyl group, an aryl group, an acyl group, a carboxyl group or a sulfo group.

In the formulae (A)–(J), M represents a transition metal such as Ni, Pd, Pt, Cu, Co, or the like, and may have a charge to form a salt with a cation, and in addition, other ligands may be bonded above or below M. Such salts may be used also as a light stabilizer. The alkyl, cyclic alkyl, aryl and heterocyclic groups and substituents therefor include those described above.

More preferable embodiments are shown in Table 2.

TABLE 2

Embodiments of metal complex-light stabilizers

| Metal Complex Nos. | Corresponding Structure | $R_a$ | $R_b$ | $R_c$ | $R_d$ | $R_e$ | $R_f$ | X | M | Counter Cation |
|---|---|---|---|---|---|---|---|---|---|---|
| 1 | (A) | Ph | Ph | — | — | — | — | — | Cu | NBu$_4$ |
| 2 | (A) | C$_4$H$_9$ | C$_4$H$_9$ | — | — | — | — | — | Ni | — |
| 3 | (B) | Cl | H | Cl | Cl | — | — | — | Ni | NBu$_4$ |
| 4 | (B) | H | OCH$_3$ | H | H | — | — | — | Cu | — |
| 5 | (C) | — | — | — | — | — | — | O | Co | NBu$_4$ |
| 6 | (C) | — | — | — | — | — | — | S | Ni | CN |
| 7 | (D) | H | OCH$_3$ | H | H | CH$_2$COOEt | — | — | Pd | NBu$_4$ |
| 8 | (D) | H | H | H | H | CH$_3$ | — | — | Ni | PBu$_4$ |
| 9 | (D) | H | CH$_3$ | H | H | CH$_3$ | — | — | Pt | NPe4 |

TABLE 2-continued

Embodiments of metal complex-light stabilizers

| Metal Complex Nos. | Corresponding Structure | $R_a$ | $R_b$ | $R_c$ | $R_d$ | $R_e$ | $R_f$ | X | M | Counter Cation |
|---|---|---|---|---|---|---|---|---|---|---|
| 10 | (E) | H | H | H | H | $CH_3$ | $CH_3$ | — | Ni | $NBu_4$ |
| 11 | (E) | H | $OCH_3$ | H | H | $C_2H_5$ | $C_2H_5$ | — | Pt | NEt4 |
| 12 | (F) | H | H | H | — | — | — | O | Cu | $NBu_4$ |
| 13 | (F) | H | H | H | — | — | — | O | Ni | $PBu_4$ |
| 14 | (F) | H | Ph | H | — | — | — | S | Ni | $NOc_4$ |
| 15 | (G) | H | H | H | H | — | — | O | Ni | $NBu_4$ |
| 16 | (G) | H | H | H | H | — | — | S | Ni | $PEt_4$ |
| 17 | (H) | Ph | Ph | — | — | — | — | — | Pd | $NBu_4$ |
| 18 | (I) | H | H | H | H | — | — | — | Ni | $NBu_4$ |
| 19 | (I) | H | $OCH_3$ | H | H | — | — | — | Ni | $PEt_4$ |
| 20 | (J) | H | H | H | H | $CH_3$ | — | — | Ni | $NBu_4$ |
| 21 | (J) | H | H | H | H | $C_4H_9$ | — | — | Ni | $PBu_4$ |
| 22 | (J) | H | $CH_3$ | H | H | $C_4H_9$ | — | — | Cu | $NOc_4$ |

Et: ethyl group, Bu: butyl group; Pe: pentyl group, Oc: octyl group, and Ph: phenyl group

2) Aromatic amine-light stabilizers (see Table 3)
Following compounds may be used.

wherein $R_g$, $R_h$, $R_i$ and $R_j$ are the same or different, and each represents a hydrogen atom, or an alkyl group optionally having a substituent, X represents an acid anion, and A is, when m is 1 or 2, wherein p is 1 or 2, and is, when m is 2, wherein all of existing aromatic rings may be substituted with an alkyl group having from 1 to 6 carbon atoms, an alkoxy group having from 1 to 6 carbon atoms, a halogen atom or a hydroxyl group.

More preferred embodiments are shown in Table 3.

TABLE 3

Embodiments of aminium, imonium and diimonium compounds

| Compound Nos. | $R_g$ | $R_h$ | $R_i$ | $R_j$ | A | X | m |
|---|---|---|---|---|---|---|---|
| 101 | $C_2H_5$ | $C_2H_5$ | $C_2H_5$ | $C_2H_5$ | Z1, p = 2 | $ClO_4$ | 1 |
| 102 | $C_2H_5$ | $C_2H_5$ | $C_2H_5$ | $C_2H_5$ | Z1, p = 1 | $SbF_6$ | 1 |
| 103 | $C_3H_7$ | $C_3H_7$ | $C_3H_7$ | $C_3H_7$ | Z1, p = 1 | Br | 1 |
| 104 | $C_3H_7$ | $C_3H_7$ | $C_3H_7$ | $C_3H_7$ | Z1, p = 2 | $PF_6$ | 1 |
| 105 | $C_4H_9$ | $C_4H_9$ | $C_4H_9$ | $C_4H_9$ | Z1, p = 1 | $ClO_4$ | 1 |
| 106 | $C_3H_7$ | H | $C_3H_7$ | H | Z1, p = 1 | $ClO_4$ | 1 |
| 107 | $C_2H_5$ | $C_2H_5$ | $C_2H_5$ | $C_2H_5$ | Z1, p = 2 | Cl | 1 |
| 108 | $C_6H_{13}$ | H | $C_6H_{13}$ | H | Z1, p = 1 | $SbF_6$ | 1 |

TABLE 3-continued

Embodiments of aminium, imonium and diimonium compounds

| Compound Nos. | $R_g$ | $R_h$ | $R_i$ | $R_j$ | A | X | m |
|---|---|---|---|---|---|---|---|
| 109 | $C_6H_{13}$ | H | $C_6H_{13}$ | H | Z1, p = 1 | $ClO_4$ | 1 |
| 110 | $C_2H_5$ | $C_2H_5$ | $C_2H_5$ | $C_2H_5$ | Z1, p = 1 | $SbF_6$ | 1 |
| 111 | $C_3H_7$ | $C_3H_7$ | $C_3H_7$ | $C_3H_7$ | Z1, p = 2 | $ClO_4$ | 1 |
| 112 | $C_2H_5$ | $C_2H_5$ | $C_2H_5$ | $C_2H_5$ | Z2 | $PF_6$ | 2 |
| 113 | $C_2H_5$ | $C_2H_5$ | $C_2H_5$ | $C_2H_5$ | Z2 | $ClO_4$ | 2 |
| 114 | $C_3H_7$ | $C_3H_7$ | $C_3H_7$ | $C_3H_7$ | Z2 | $SbF_6$ | 2 |
| 115 | $C_3H_7$ | H | $C_3H_7$ | H | Z2 | $AsF_6$ | 2 |
| 116 | $C_4H_9$ | $C_4H_9$ | $C_4H_9$ | $C_4H_9$ | Z2 | I | 2 |
| 117 | $C_6H_{13}$ | H | $C_6H_{13}$ | H | Z2 | $ClO_4$ | 2 |

Z1:

Z2:

c. Undercoat Layer

The undercoat layer is used for the purpose of (1) an improvement of adherability, (2) a barrier against water, gases, or the like, (3) an improvement of the storage stability of the recording layer, (4) an enhancement of the reflectance, (5) a protection of the substrate from a solvent, (6) a formation of a guiding groove, guiding pit or preformat, or the like. With regard to the purpose of (1), macromolecular materials, for example, various polymers such as ionomer resin, polyamide resin, vinyl resin, natural resin, natural polymer, silicone, liquid rubber, silane coupling agents, or the like may be used. With regard to the purposes of (2) and. (3), in addition to the aforementioned macromolecular materials, inorganic compounds such as SiO, MgF, $SiO_2$, TiO, ZnO, TiN, SiN, or the like, and further metals or semimetals such as Zn, Cu, Ni, Cr, Ge, Se, Au, Ag, Al, or the like may be used. Moreover, with regard to the purpose of (4), metals such as Al, Au, Ag, or the like, or organic films having metallic luster such as a methine dye, a xanthene dye, or the like may be used. With regard to the purposes of (5) and (6), a ultraviolet-curing resin, a thermosetting resin, a: thermoplastic resin, or the like may be used.

The membrane thickness of the undercoat layer is preferably 0.01–30 µm, more preferably 0.05–10 µm.

d. Metal Refractive Layer

Examples of the material for the metal refractive layer include poorly erodable metals, semimetals, and the like exhibiting a high reflectance themselves. Embodiments of the material for the metal refractive layer include Au, Ag, Cr, Ni, Al, Fe, Sn, and the like, but Au, Ag and Al are most preferred from a viewpoint of the reflectance and productivity. These metals or semimetals may be used alone or as an alloy of two of them.

The method for forming a membrane includes a vapor deposition, a sputtering, and the like. The membrane thickness of the metal refractive layer is preferably 50–5,000 Å, more preferably 100–3,000 Å.

e. Protective Layer, Substrate Surface-hard Coating Layer

A protective layer and a substrate surface-hard coating layer are used for the purpose of (1) a protection of the recording layer (refraction absorbing layer) from flaw, dust, dirt or the like., (2) an improvement in the storage stability of the recording layer (refraction absorbing layer), (3) an improvement in the reflectance, or the like. With regard to such purposes, the materials described for the undercoat layer may be used. In addition, SiO, $SiO_2$ or the like may be used as an: inorganic material, and thermo-softening resins such as polymethyl acrylate, polycarbonate, polystyrene, polyester, vinyl resin, cellulose, aliphatic hydrocarbons, natural rubber, styrene-butadiene, chloroprene rubber, wax, alkyd, drying oil, or rosin, thermosetting resins such as epoxy resin, phenol resin, polyurethane resin, melamine resin, or urea resin, ultraviolet-curing resins such as polyester acrylate, epoxy acrylate, urethane acrylate, or silicone acrylate, or the like may be used as an organic material, but among them, the ultraviolet-curing resins may be preferably used in that they have the excellent productivity.

The membrane thickness of the protective layer or the substrate surface-hard coating layer is preferably 0.01–30 µm, more preferably 0.05–10 µm. In the present invention, stabilizers, dispersing agents, flame retardants, lubricants, antistatic agents, surfactants, plasticizers or the like may be incorporated into the above undercoat layer, protective layer and substrate surface-hard coating layer as described for the recording layer.

f. Protective Substrate

A protective substrate should be transmittable to the wavelength of the laser beam to be used when the laser beam is irradiated from this protective substrate side, whereas it may be transmittable or not to the wavelength when it is used as a mere protective plate. The materials which may be used for the protective substrate are the same as those for the substrate, and plastics such as polyester, acrylic resin, polyamide, polycarbonate resin, polyolefin resin, phenol resin, epoxy resin, or polyimide, or the like, glasses, ceramics, metals, or the like may be used.

g. Adhesive, Adhesive Layer

As the adhesive, any material which can adhere two recording media may be used, but from a viewpoint of the productivity, ultraviolet-curing or hot melt adhesives are preferred.

EXAMPLE

The following Examples further illustrate the present invention, but are not to be construed to limit the scope of the present invention.

Example 1

1.62 g of 3,4-dichloro-3-cyclobutene-1,2-dione was dissolved in 16.5 ml of dichloromethane. To this solution, 3.72 g of 1,3,3-trimethyl-2-methyleneindoline was added dropwise at 4° C., and the mixture was stirred at 4° C. for 1.5 hours. After the reaction, the precipitate was collected by filtration. The obtained solid was added to a mixture of 9 g of trifluoroacetic acid and 0.14 g of water, and the mixture was allowed to react at 45° C. for 1 hour. After the reaction was completed, the volatile component was distilled off with a rotary evaporator. To the residue, acetone was added, and the mixture was heated with stirring, and then the insoluble material was collected by filtration. To this insoluble material, 60 ml of n-butanol, 60 ml of toluene and 1.3 g of 3-methyl-1-phenyl-2-pyrazolin-5-one were added, and the mixture was allowed to react at 110° C. for 2 hours. After the reaction was completed, the precipitate was collected by filtration to give 1.68 g of the compound 1.

Melting point: 262–264° C.; Elemental analysis ($C_{26}H_{23}N_3O_3$): Calcd. (%): C, 73.39; H, 5.45; N, 9.88; Found (%): C, 73.11; H, 5.41; N, 9.66; IR (KBr) cm$^{-1}$: 3442, 1761, 1635, 1481, 1462, 1444, 1302, 1242, 1094, 1045, 941, 797; $^1$H-NMR δ ($CDCl_3$) ppm: 1.74 (6H, s), 2.59 (3H, s), 3.67 (3H, s), 5.85 (1H, s), 7.13 (1H, m), 7.26 (2H, m), 7.41 (4H, m), 7.86 (2H, m).

Example 2

In a manner similar to that in Example 1 except that 2.6 g of 5-methoxy-1,3,3-trimethyl-2-methyleneindoline was used instead of 1,3,3-trimethyl-2-methyleneindoline, 1.1 g of the compound 2 was obtained.

Melting point: 249–251° C.; Elemental analysis ($C_{27}H_{25}N_3O_4$): Calcd. (%): C, 71.19; H, 5.53; N, 9.22; Found (%): C, 70.90; H, 5.52; N, 9.11; IR (KBr) cm$^{-1}$: 3477, 1753, 1632, 1508, 1462, 1304, 1242, 1099, 1016, 945, 787; $^1$H-NMR δ ($CDCl_3$) ppm: 1.74 (6H, s), 2.59 (3H, s), 3.67 (3H, s), 3.86 (3H, s), 5.82 (1H, s), 6.90 (1H, m), 6.96 (1H, m), 7.06 (1H, m), 7.25 (1H, m), 7.42 (2H, m), 7.85 (2H, m).

Example 3

8.99 g of 3,4-dichloro-3-cyclobutene-1,2-dione was dissolved in 59 ml of dichloromethane. To this solution, 10.91 g of 3-methyl-1-phenyl-2-pyrazolin-5-one was added dropwise at room temperature, and the mixture was stirred at room temperature for 70 hours. After the reaction, the precipitate was filtered off. The mother liquid was concentrated, and 32 ml of acetic acid and 32 ml of water were added to the concentrate, and the mixture was allowed to react at 100° C. for 1.5 hours. After the reaction was completed, the precipitate was collected by filtration. To this, 25 ml of n-butanol, 25 ml of toluene and 0.41 g of 5-chloro-1,3,3-trimethyl-2-methyleneindoline were added, and the mixture was allowed to react at 110° C. for 1.5 hours. After the reaction was completed, the precipitate was collected by filtration to give 0.77 g of the compound 3.

Melting point: 283–285° C.; Elemental analysis ($C_{26}H_{22}ClN_3O_3$): Calcd. (%): C, 67.90; H, 4.82; N, 9.14; Found (%): C, 67.91; H, 4.69; N, 9.12; IR (KBr) cm$^{-1}$: 3448, 1765, 1641, 1452, 1300, 1236, 1094, 1041; $^1$H-NMR δ ($CDCl_3$) ppm: 1.74 (6H, s), 2.58 (3H, s), 3.62 (3H, s), 5.79 (1H, s), 7.02 (1H, m), 7.26 (1H, m), 7.35 (2H, m), 7.43 (2H, m), 7.86 (2H, m).

Example 4

In a manner similar to that in Example 1 except that 2.08 g of 3-methyl-1-p-methoxyphenyl-2-pyrazolin-5-one was used instead of 3-methyl-1-phenyl-2-pyrazolin-5-one, 1.1 g of the compound 4 was obtained.

Melting point: 247–249° C.; Elemental analysis ($C_{27}H_{25}N_3O_4$): Calcd. (%): C, 71.19; H, 5.53; N, 9.22; Found (%): C, 71.28; H, 5.66; N, 9.01; IR (KBr) cm$^{-1}$: 2927, 1753, 1628, 1481, 1437, 1302, 1242, 1155, 1097, 1072, 1045; $^1$H-NMR δ (CDCl$_3$) ppm: 1.74 (6H, s), 2.58 (3H, s), 3.67 (3H, s), 3.83 (3H, s), 5.85 (1H, s), 6.95 (2H, m), 7.13 (1H, m), 7.27 (1H, m), 7.39 (2H, m), 7.73 (2H, m).

Example 5

In a manner similar to that in Example 1 except that 1.42 g of 3-methyl-1-m-methylphenyl-2-pyrazolin-5-one was used instead of 3-methyl-1-phenyl-2-pyrazolin-5-one, 2.5 g of the compound 5 was obtained.

Melting point: 250° C.; Elemental analysis ($C_{27}H_{25}N_3O_3$): Calcd. (%): C, 73.79; H, 5.73; N, 9.56; Found (%): C, 73.66; H, 5.81; N, 9.58; IR (KBr) cm$^{-1}$: 3435, 1755, 1633, 1483, 1305, 1244, 1095, 1046; $^1$H-NMR δ (CDCl$_3$) ppm: 1.74 (6H, s), 2.41 (3H, s), 2.59 (3H, s), 3.68 (3H, s), 5.85 (1H, s), 7.08 (1H, m), 7.13 (1H, m), 7.28 (1H, m), 7.39 (2H, m), 7.66 (1H, m), 7.67 (1H, m).

Example 6

In a manner similar to that in Example 1 except that 1.42 g of 3-methyl-1-p-methylphenyl-2-pyrazolin-5-one was used instead of 3-methyl-1-phenyl-2-pyrazolin-5-one, 1.74 g of the compound 6 was obtained.

Melting point: 253° C.; Elemental analysis ($C_{27}H_{25}N_3O_3$): Calcd. (%): C, 73.79; H, 5.73; N, 9.56; Found (%): C, 73.74; H, 5.60; N, 9.51; IR (KBr) cm$^{-1}$: 3435, 2927, 1755, 1630, 1481, 1466, 1304, 1242, 1124, 1070, 1045; $^1$H-NMR δ (CDCl$_3$) ppm: 1.74 (6H, s), 2.37 (3H, s), 2.58 (3H, s), 3.67 (3H, s), 5.84 (1H, s), 7.13 (1H, m), 7.23 (2H, m), 7.27 (1H, m), 7.39 (1H, m), 7.41 (1H, m), 7.72 (1H, m).

Example 7

In a manner similar to that in Example 1 except that 2.15 g of 1-(4-nitrophenyl)-3-pyrrolidino-2-pyrazolin-5-one was used instead of 3-methyl-1-phenyl-2-pyrazolin-5-one, 2.76 g of the compound 7 was obtained.

Melting point: 254° C.; Elemental analysis ($C_{29}H_{27}N_5O_5$): Calcd. (%): C, 66.27; H, 5.18; N, 13.33; Found (%): C, 65.98; H, 5.32; N, 13.05; IR (KBr) cm$^{-1}$: 3440, 2968, 1759, 1510, 1475, 1454, 1290, 1238, 1165, 1107, 1064; $^1$H-NMR δ (CDCl$_3$) ppm: 1.71 (6H, s), 1.98 (4H, t, J=6.6 Hz), 3.61 (3H, s), 3.69 (4H, t, J=6.6 Hz), 5.70 (1H, s), 7.08 (1H, m), 7.24 (1H, m), 7.37 (2H, m), 8.21 (2H, m), 8.25 (2H, m).

Example 8

1.51 g of 3,4-dichloro-3-cyclobutene-1,2-dione was dissolved in 10 ml of ethyl acetate. To this solution, 3.26 g of 1,1,3-trimethyl-2-methylenebenz[e]indoline was added dropwise at 4° C., and the mixture was stirred at 4° C. for 2 hours. After the reaction, the precipitate was collected by filtration. The obtained solid was added to 9.1 g of trifluoroacetic acid and 0.15 g of water, and the mixture was allowed to react at 45° C. for 3 hours. After the reaction was completed, the volatile component was distilled off with a rotary evaporator. To the residue, acetone was added. The mixture was heated and then the insoluble material collected by filtration. To this insoluble material, 30 ml of n-butanol, 30 ml of toluene and 1.36 g of 3-methyl-1-phenyl-2-pyrazolin-5-one were added, and the mixture was allowed to react at 110° C. for 2 hours. After the reaction was completed, the precipitate was collected by filtration to give 2.42 g of the compound 8.

Melting point: 280° C. or above (dec.); Elemental analysis ($C_{30}H_{25}N_3O_3$): Calcd. (%): C, 75.77; H, 5.30; N, 8.84; Found (%): C, 75.80; H, 5.52; N, 8.76; IR (KBr) cm$^{-1}$: 1524, 1497, 1471, 1460, 1435, 1304, 1265, 1097; $^1$H-NMR δ (CDCl$_3$) ppm: 2.01 (6H, s), 2.61 (3H, s), 3.81 (3H, s), 5.92 (1H, s), 7.2–8.3 (11H, m).

Example 9

In a manner similar to that in Example 8 except that 4.75 g of 3-ethyl-1,1-dimethyl-2-methylenebenz[e]indoline was used instead of 1,1,3-trimethyl-2-methylenebenz[e]indoline, 2.75 g of the compound 9 was obtained.

Melting point: 221° C.; Elemental analysis ($C_{31}H_{27}N_3O_3$): Calcd. (%): C, 76.05; H, 5.56; N, 8.58; Found (%): C, 75.94; H, 5.54; N, 8.57; IR (KBr) cm$^{-1}$: 1525, 1497, 1468, 1450, 1437, 1333, 1300, 1255, 1209, 1095, 1020; $^1$H-NMR δ (CDCl$_3$) ppm: 1.50 (3H, t, J=7.3 Hz), 2.03 (6H, s), 2.62 (3H, s), 4.2–4.4 (2H, m), 5.96 (1H, s), 7.3–8.3 (11H, m).

Example 10

The maximum absorption wavelength ($\lambda_{max}$) and the log ε (ε is a molar extinction coefficient) at the maximum absorption wavelength for a chloroform solution of the prepared compound 1–3, 5, 6, 8, 10–15 or 17 were measured. The results are shown in Table 4 (Compounds 10–15 and 17 were prepared in Examples 22–27 and 29 below, respectively).

Example 11

T1, T2, (m1−m2)(%)/(T2−T1)(° C.) and (m1−m2)(%) for the compounds 1–3, 5, 6, 8, 10–15 and 17 measured with TG-DTA (a thermogravimetric-differential thermal analyzer) are shown in Table 4 (Compounds 10–1 5 and 17 were prepared in Examples 22–27 and 29 below, respectively).

Comparative Example

The spectroscopic (maximum absorbing wavelength and molar extinction coefficient) and thermal decomposition properties (weight losing-initiation temperature, weight losing-termination temperature, ratio of the loss in weight, and temperature slope of the loss in weight) which were measured for the squarylium compounds represented by the following formulae (a), (b) and (c) in a procedure similar to those in Examples 10 and 11 are shown in Table 4. The compounds (a) and (b) were synthesized according to the procedure described in *Angew. Chem. Int. Ed. Engl.* 7(7), 530–535 (1968), and the compound (c) was synthesized according to the procedure described in Japanese Unexamined Patent Publication 339233/1993.

(a)

-continued

TABLE 4

Spectroscopic and thermal decomposition properties of squarylium compounds

| | Spectroscopic properties (chloroform solution) | | Thermal decomposition properties | | | |
|---|---|---|---|---|---|---|
| | $\lambda_{max}$ (nm) | log ε | T1 (° C.) | T2 (° C.) | $\frac{(m1-m2)(\%)}{(T2-T1)(° C.)}$ | (m1 − m2) (%) |
| Compound | | | | | | |
| 1 | 571 | 5.2 | 279.1 | 301.1 | 1.3 | 27.8 |
| 2 | 583.5 | 5.2 | 282.2 | 301.3 | 1.4 | 26.6 |
| 3 | 576.5 | 5.3 | 302.9 | 316.9 | 2.6 | 36.3 |
| 5 | 571.5 | 5.2 | 297.0 | 316.0 | 1.8 | 33.2 |
| 6 | 571.5 | 5.2 | 281.7 | 303.6 | 1.4 | 30.4 |
| 8 | 589.5 | 5.2 | 291.2 | 301.3 | 2.1 | 21.2 |
| 10 | 564.5 | 5.3 | 260.7 | 298.9 | 1.1 | 41.4 |
| 11 | 563.0 | 5.0 | 274.3 | 290.1 | 1.4 | 22.2 |
| 12 | 559.5 | 5.1 | 265.7 | 279.5 | 1.6 | 22.4 |
| 13 | 573.5 | 5.4 | 268.3 | 289.5 | 1.5 | 31.7 |
| 14 | 567.0 | 5.3 | 268.3 | 289.5 | 1.5 | 31.7 |
| 15 | 571.5 | 5.3 | 259.0 | 293.0 | 1.6 | 34.0 |
| 17 | 569.0 | 5.1 | 274.1 | 297.1 | 1.5 | 35.4 |
| Comparative Examples | | | | | | |
| a | 509 | 5.0 | 319.9 | 334.3 | 1.8 | 26.4 |
| b | 633 | 5.5 | 328.8 | 337.1 | 5.2 | 43.3 |
| c | 598 | 4.8 | 308.4 | 327.5 | 1.5 | 27.8 |

Examples relating to the optical recording media will be illustrated below.

Example 12

A solution prepared by dissolving the compound 1 in 2,2,3,3-tetrafluoro-1-propanol was spinner-coated on an injection molded-polycarbonate substrate of 0.6 mm thickness having a guiding groove of the groove depth of 1,750 Å, the half band width of 0.25 μm, and the track pitch of 0.74 μm to form an organic dye layer having the thickness of 900 Å. The optical constants of the resulting recording membrane are shown in Table 5. In the table, n represents a refractive index of the single layer of the recording layer, and k represents an extinction coefficient.

Then, a gold refractive layer having the thickness of 1,200 Å was provided thereon by a sputtering method, a protective layer having the thickness of 7 μm was further provided thereon with an acrylic photopolymer, and then an injection molded-polycarbonate flat substrate having the thickness of 0.6 mm was adhered thereto with an acrylic photopolymer to prepare a recording medium.

An EFM signal was recorded on the prepared recording medium with tracking (linear speed of 3.5 m/sec.) using the semiconductor laser beam having an oscillation wavelength of 650 nm and a beam diameter of 1.0 μm, and then the recorded signal was reproduced with a continuous beam of the semiconductor laser having an oscillation wavelength of 650 nm (reproduction power of 0.7 mW). The resulting signal properties are shown in Table 6.

Examples 3–17

The recording membrane was formed in a manner completely similar to that in Example 12 except that the compound 2, 4, 5, 6 or 9 was used instead of the compound 1 (Examples 13–17). The optical constants of the resulting recording membrane are shown in Table 5. Furthermore, the recording medium was formed in a manner completely similar to that in Example 12 and the signal properties thereof were measured. The resulting signal properties are shown in Table 6.

TABLE 5

Optical constants of recording membrane

| | λ = 635 nm | | λ = 650 nm | |
|---|---|---|---|---|
| | n | k | n | k |
| Example 12 | 2.81 | 0.31 | 2.57 | 0.10 |
| Example 13 | 2.83 | 0.57 | 2.72 | 0.24 |
| Example 14 | 2.88 | 0.28 | 2.60 | 0.07 |
| Example 15 | 2.78 | 0.33 | 2.55 | 0.12 |
| Example 16 | 2.96 | 0.12 | 2.59 | 0.05 |
| Example 17 | 2.93 | 0.34 | 2.72 | 0.13 |
| Example 30 | 2.73 | 0.25 | 2.48 | 0.08 |
| Example 31 | 2.49 | 0.12 | 2.31 | 0.04 |
| Example 32 | 2.52 | 0.05 | 2.37 | 0.03 |
| Example 33 | 2.75 | 0.18 | 2.48 | 0.04 |
| Example 34 | 2.72 | 0.25 | 2.50 | 0.07 |
| Example 35 | 2.59 | 0.15 | 2.36 | 0.07 |
| Example 36 | 2.58 | 0.07 | 2.39 | 0.02 |
| Example 37 | 2.62 | 0.16 | 2.39 | 0.05 |

TABLE 6

Signal properties of recording medium

| | Reflectance (%): flat portion | Modulation depth (%): $I_{11}I_{top}$ | Jitter (%) |
|---|---|---|---|
| Example 12 | 65.4 | 62.2 | 8.4 |
| Example 13 | 64.9 | 61.0 | 9.0 |
| Example 14 | 63.9 | 63.0 | 8.7 |
| Example 15 | 64.5 | 61.5 | 8.6 |
| Example 16 | 65.1 | 62.0 | 8.9 |
| Example 17 | 64.7 | 63.1 | 8.8 |
| Example 30 | 62.4 | 62.1 | 8.3 |
| Example 31 | 60.2 | 65.7 | 8.4 |
| Example 32 | 64.5 | 62.3 | 8.5 |
| Example 33 | 65.4 | 60.9 | 8.6 |
| Example 34 | 63.1 | 61.5 | 8.7 |
| Example 35 | 61.1 | 62.3 | 8.9 |
| Example 36 | 60.3 | 64.1 | 8.9 |
| Example 37 | 62.5 | 62.4 | 8.8 |

Signal properties of the high reflectance, high modulation depth and low jitter that are conformable to DVD-R standard proposal were obtained.

Example 18

A recording medium was formed using a mixture of the compound 1 and the metal complex No. 3 (see Table 2;

weight ratio of compound 1/metal complex No. 3=10/3) instead of the compound in Example 12.

The recording medium was irradiated with the light from a xenon lamp (50,000 luxes) for 10 hours, and a remaining ratio of an optical density was evaluated. The remaining ratio of an optical density was calculated by the following equation:

Remaining ratio of an optical density=$I_d/I_o \times 100$ (%)

$I_d$: Optical density after irradiation;
$I_0$: Optical density before irradiation.

The results of the light resistance test are shown in Table 7.

Examples 19–21

The recording layer was formed, using the aromatic amine compound No. 104 (see Table 13) instead of the metal complex No. 3 (Example 19), and further using a mixture of the compound 4 and the metal complex No. 12 (see Table 2)(Example 20) or a mixture of the compound 4 and the aromatic amine compound No. 113 (see Table 3)(Example 21) instead of a mixture of the compound 1 and the metal complex No. 3 in Example 18. A light resistance test was performed on the resulting recording layer in a manner similar to that in Example 18. The results of the light resistance test are shown in Table 7.

TABLE 7

Results of light resistance test of recording layer

| | Compound Nos. | Light stabilizer Nos. | Remaining ratio of Optical density (%) |
|---|---|---|---|
| Example 18 | 1 | 3 | 84 |
| Example 19 | 1 | 104 | 91 |
| Example 20 | 4 | 12 | 88 |
| Example 21 | 4 | 113 | 92 |

Example 22

2.65 g of 3,4-dichloro-3-cyclobutene-1,2-dione was dissolved in 35 ml of dichloromethane. To this solution, 7.54 g of 1-butyl-3,3-dimethyl-2-methyleneindoline was added dropwise at 4° C., and the mixture was stirred at 4° C. for 1 hour. After the reaction, the reaction mixture was washed with water, and the volatile component was distilled off from the organic layer with a rotary evaporator. To the residue, 20 ml of methanol and 20 ml of t-butyl methyl ether were added. After the mixture was heated with stirring for 1 hour, the insoluble material was collected by filtration. The obtained solid was added to a mixture of 0.43 g of trifluoroacetic acid and 0.14 g of water, and the mixture was allowed to react at 45° C. for 1 hour. After the reaction was completed, the volatile component was distilled off with a rotary evaporator. To the residue, 13 ml of n-butanol, 13 ml of toluene and 0.73 g of 1,3-dimethyl-2-pyrazolin-5-one were added, and the mixture was allowed to react at 110° C. for 5 hours. After the reaction was completed, the volatile component was distilled off with a rotary evaporator. To the residue, 3 ml of ethanol and 1 ml of chloroform were added, and the mixture was heated with stirring for 1 hour. After the mixture was cooled to room temperature, the insoluble material was collected by filtration to give 1.23 g of the compound 10.

Melting point: 188–191° C.; Elemental analysis ($C_{24}H_{27}N_3O_3$): Calcd. (%): C, 71.09; H, 6.71; N, 10.36; Found (%): C, 70.84; H, 6.65; N, 10.20; IR (KBr) cm$^{-1}$: 1747, 1612, 1441, 1302, 1186, 1088, 1068, 1016; $^1$H-NMR δ (CDCl$_3$) ppm: 1.01 (3H, t, J=7.3 Hz), 1.47 (2H, qt, J=7.3, 7.6 Hz), 1.76 (6H, s), 1.81 (2H, tt, J=7.6, 7.8 Hz), 2.51 (3H, s), 3.55 (3H, s), 4.07 (2H, t, J=7.8 Hz), 5.90 (1H, s), 7.11 (1H, m), 7.27 (1H, m), 7.39 (2H, m).

Example 23

0.54 g of 3,4-dichloro-3-cyclobutene-1,2-dione was dissolved in 13 ml of ethyl acetate. To this solution, 1.24 g of 1,3,3-trimethyl-2-methyleneindoline was added dropwise at room temperature, and the mixture was stirred at room temperature for 1 hour. After the reaction, the precipitate was collected by filtration. The obtained solid was added to a mixture of 1.8 g of trifluoroacetic acid and 60 mg of water, and the mixture was allowed to react at 45° C. for 1 hour. After the reaction was completed, the volatile component was distilled off with a rotary evaporator. To the residue, 6 ml of acetone was added. After the mixture was stirred at room temperature for 1 hour, the insoluble material was collected by filtration. To this insoluble material, 25 ml of n-butanol, 25 ml of toluene and 0.69 g of 1-phenyl-3-trifluoromethyl-2-pyrazolin-5-one were added, and the mixture was allowed to react at 110° C. for 15 hours. After the reaction was completed, the precipitate was collected by filtration to give 0.48 g of the compound 11.

Melting point: 268–269° C.; Elemental analysis ($C_{26}H_{20}N_3O_3F_3$): Calcd. (%): C, 65.13; H, 4.20; N, 8.76; Found (%): C, 65.29; H, 4.22; N, 8.63; IR (KBr) cm$^{-1}$: 3446, 2933, 1761, 1635, 1477, 1454, 1315, 1227, 1183, 1130, 1068, 989; $^1$H-NMR δ (CDCl$_3$) ppm: 1.75 (6H, s), 3.81 (3H, s), 5.98 (1H, s), 7.25 (1H, m), 7.33 (1H, m), 7.38 (1H, m), 7.43–7.49 (4H, m), 7.86 (2H, m).

Example 24

1.99 g of 3,4-dichloro-3-cyclobutene-1,2-dione was dissolved in 44 ml of ethyl acetate. To this solution, 4.57 g of 1,3,3-trimethyl-2-methyleneindoline was added dropwise at room temperature, and the mixture was stirred at room temperature for 1 hour. After the reaction, the precipitate was collected by filtration. The obtained solid was added to a mixture of 5.81 g of trifluoroacetic acid and 0.18 g of water, and the mixture was allowed to react at 45° C. for 1 hour. After the reaction was completed, the volatile component was distilled off with a rotary evaporator. To the residue, 22 ml of acetone was added. The mixture was stirred at room temperature for 1 hour and the insoluble material was collected by filtration. To this insoluble material, 20 ml of n-butanol, 20 ml of toluene and 1.26 g of 3-n-propyl-2-pyrazolin-5-one were added, and the mixture was allowed to react at 110° C. for 5 hours. After the reaction was completed, the volatile component was distilled off with a rotary evaporator, and the residue was purified by subjecting it to column chromatography (silica gel: eluent chloroform/methanol=15/1) to give 0.94 g of the compound 12.

Melting point: 252.8–253.3° C. (dec.); Elemental analysis ($C_{22}H_{23}N_3O_3$): Calcd. (%): C, 70.01; H, 6.14; N, 11.13; Found (%): C, 69.81; H, 6.05; N, 10.91; IR (KBr) cm$^{-1}$: 3446, 2933, 1761, 1635, 1477, 1454, 1315, 1227, 1183, 1130, 1068, 989; $^1$H-NMR δ (CDCl$_3$) ppm: 1.02 (3H, t, J=7.56 Hz), 1.76 (6H, s), 1.77 (2H, m), 3.08 (2H, t, J=7.57 Hz), 3.77 (3H, s), 6.05 (1H, s), 7.18 (1H, m), 7.29 (1H, m), 7.33 (1H, m), 7.44 (1H, m).

Example 25

1.45 g of 3,4-dimethoxy-3-cyclobutene-1,2-dione and 1.42 g of potassium carbonate were added to 10 ml of methanol. To this solution, 2.06 g of 1-phenyl-3-isopropyl-2-pyrazolin-5-one which had been dissolved in 15 ml of methanol was added dropwise at room temperature. The mixture was stirred at room temperature for 1 hour. After the reaction, the precipitate was collected by filtration. The obtained solid was added to 50 ml of water, and after a pH of the mixture was adjusted to 3 with hydrochloric acid (concentration of 1 mol/L), the insoluble material was collected by filtration. The obtained solid was added to a mixture of 4 ml of hydrochloric acid (concentration of 1 mol/L) and 32 ml of dimethylformamide, and the mixture was heated at 45° C. for 1 hour. After the reaction, 79 ml of water was added to the mixture. The mixture was stirred at 10° C. for 30 minutes and the insoluble material was collected by filtration. To this insoluble material, 15 ml of n-butanol, 15 ml of toluene and 1.22 g of 1,3,3-trimethyl-2-methyleneindoline were added, and the mixture was allowed to react at 110° C. for 8 hours. After the reaction was completed, the volatile component was distilled off with a rotary evaporator, and 15 ml of ethanol was added to the residue. After the mixture was heated for 1 hour, the insoluble material was collected by filtration to give 2.97 g of the compound 13.

Melting point: 210–212° C. (dec.); Elemental analysis ($C_{28}H_{27}N_3O_3$): Calcd. (%): C, 74.15; H, 6.00; N, 9.27; Found (%): C, 74.11; H, 5.90; N, 9.17; IR (KBr) cm$^{-1}$: 3434, 2964, 1759, 1637, 1479, 1450, 1311, 1242, 1159, 1072; $^1$H-NMR δ (CDCl$_3$) ppm: 1.37 (6H, d, J=6.8 Hz), 1.74 (6H, s), 3.65 (3H, sept, J=6.8 Hz), 5.83 (1H, s), 7.12 (1H, m), 7.25 (2H, m), 7.40 (4H, m), 7.89 (2H, m).

Example 26

1.45 g of 3,4-dimethoxy-3-cyclobutene-1,2-dione and 1.42 g of potassium carbonate were added to 10 ml of methanol. To this solution, 1.14 g of 1,3-dimethyl-2-pyrazolin-5-one which had been dissolved in 15 ml of methanol was added dropwise at room temperature, and the mixture was stirred at room temperature for 1 hour. After the reaction, the precipitate was collected by filtration. The obtained solid was added to 20 ml of water, and after 15 ml of hydrochloric acid: (concentration of 1 mol/L) was added to the mixture, the insoluble material was collected by filtration. The obtained solid was added to a mixture of 11 ml of hydrochloric acid (concentration of 1 mol/L) and 35 ml of dimethylformamide, and the mixture was allowed to react at room temperature for 1 hour. After the reaction, the insoluble material was collected by filtration. To this insoluble material, 15 ml of n-butanol, 15 ml of toluene, 2.73 g of 1',2'-dimethylspiro[cyclohexyl-1,3'-3H-indolium] iodide and 1.1 g of quinoline were added, and the mixture was allowed to react at 110° C. for 8 hours. After the reaction was completed, the volatile component was distilled off with a rotary evaporator. To the residue, 20 ml of ethanol was added. The mixture was heated for 1 hour, and the insoluble material was collected by filtration to give 1.99 g of the compound 14.

Melting point: 251–252° C. (dec.); Elemental analysis ($C_{24}H_{25}N_3O_3$): Calcd. (%): C, 71.44; H, 6.25; N, 10.41; Found (%): C, 71.13; H, 6.17; N, 10.41; IR (KBr) cm$^{-1}$: 3437, 2912, 1745, 1624, 1502, 1477, 1448, 1311, 1200, 1092; $^1$H-NMR δ (CDCl$_3$) ppm: 1.46 (2H, m), 1.95 (6H, m), 2.36 (2H, m), 2.50 (3H, s), 3.54 (3H, s), 3.79 (3H, s), 5.81 (1H, s), 7.20 (1H, m), 7.25 (1H, m), 7.44 (1H, m), 7.88 (1H, m).

Example 27

0.92 g of 3,4-dimethoxy-3-cyclobutene-1,2-dione and 0.9 g of potassium carbonate were added to 25 ml of methanol. To this solution, 1 g of 1 -t-butyl-3-methyl-2-pyrazolin-5-one was added, and the mixture was stirred at room temperature for 2 hours. After the reaction, the precipitate was collected: by filtration. The obtained solid was added to 50 ml of water. After a pH of the mixture was adjusted to 3 with hydrochloric acid (concentration of 1 mol/L), the insoluble material was collected by filtration. The obtained solid was added to a mixture of 1 ml of hydrochloric acid (concentration of 1 mol/L) and 15 ml of dimethylformamide, and the mixture was heated at 40° C. for 2 hours. After the reaction, 79 ml of water was added to the mixture and the insoluble material was collected by filtration. To this insoluble material, 10 ml of n-butanol, 10 ml of toluene, and 0.67 g of 5-chloro-1,3,3-trimethyl-2-methyleneindoline were added, and the mixture was allowed to react at 110° C. for 3 hours. After the reaction was completed, the volatile component was distilled off with a rotary evaporator, and the residue was purified by subjecting it to column chromatography (silica gel; eluent chloroform/methanol=15/1) to give 0.82 g of the compound 15.

Melting point: 259 C (dec.); Elemental analysis ($C_{24}H_{26}N_3O_3$): Calcd. (%): C, 65.52; H, 5.96; N, 9.55; Found (%): C, 65.40; H, 5.77; N, 9.41; IR (KBr) cm$^{-1}$: 1734, 1618, 1471, 1419, 1369, 1272, 1101, 1024; $^1$H-NMR δ (CDCl$_3$) ppm: 1.57 (9H, s), 1.72 (6H, s), 2.50 (3H, s), 3.59 (3H, s), 5.79 (1H, s), 6.98–7.00 (2H, m), 7.32–7.34 (2H, m).

Example 28

2.34 g of 3,4-dimethoxy-3-cyclobutene-1,2-dione and 2.27 g of potassium carbonate were added to 26 ml of methanol. To this solution, 2.64 g of 3-phenyl-2-pyrazolin-5-one was added. The mixture was stirred at room temperature for 2 hours. After the reaction, the precipitate was collected by filtration. The obtained solid was added to 50 ml of water. After a pH of the mixture was adjusted to 3 with hydrochloric acid (concentration of 1 mol/L), the insoluble material was collected by filtration. The obtained solid was added to a mixture of 6 ml of hydrochloric acid (concentration of 1 mol/L) and 33 ml of dimethylformamide, and the mixture was heated at 75° C. for 1 hour. After the reaction, 66 ml of water was added to the mixture and the insoluble material was collected by filtration. To this insoluble material, 15 ml of n-butanol, 15 ml of toluene, and 0.52 g of 1,3,3-trimethyl-2-methyleneindoline were added, and the mixture was allowed to react at 110° C. for 5 hours. After the reaction was completed, the insoluble material was removed by filtration. Then, the volatile component was distilled off from the mother liquid with a rotary evaporator. To the residue, 12 ml of acetone and 2 ml of ethyl acetate were added and the mixture was heated. After cooling the mixture, the precipitate was collected by filtration to give 0.77 g of the compound 16.

Melting point: 251.7–252.5° C. (dec.); Elemental analysis ($C_{25}H_{21}N_3O_3$): Calcd. (%): C, 72.98; H, 5.14; N, 10.21; Found (%): C, 72.72; H, 5.11; N, 10.12; IR (KBr) cm$^{-1}$: 1508, 1477, 1448, 1311, 1278, 1242, 1159, 1072, 974; $^1$H-NMR δ (CDCl$_3$) ppm: 1.69 (6H, s), 3.84 (3H, s), 6.05 (1H, s), 7.43–7.69 (9H, m).

Example 29

1 g of 3,4-dimethoxy-3-cyclobutene-1,2-dione and 0.98 g of potassium carbonate were added to 13 ml of methanol. To this solution, 0.99 g of 1-methyl-3-n-propyl-2-pyrazolin-5-one was added, and the mixture was stirred at room temperature for 2 hours. After the reaction, 47 ml of t-butyl methyl ether was added to the mixture, and the precipitate was collected by filtration. The obtained solid was added to 35 ml of water. After a pH of the mixture was adjusted to 3 with hydrochloric acid (concentration of 1 mol/L), the insoluble material was collected by filtration. The obtained solid was added to a mixture of 2 ml of hydrochloric acid (concentration of 1 mol/L) and 12 ml of dimethylformamide, and the mixture was allowed to react at 30° C. for 1 hour. After the reaction, 24 ml of water was added to the mixture, and the insoluble material was collected by filtration. To this insoluble material, 20 ml of n-butanol, 20 ml of toluene and 0.69 g of 5-methyl-1,3,3-trimethyl-2-methyleneindoline were added, and the mixture was allowed to react at 110° C. for 3 hours.

After the reaction was completed, the volatile component was distilled off with a rotary evaporator. To the residue, 15 ml of ethanol was added and the mixture was heated. After cooling the mixture, the precipitate was collected by filtration to give 1.37 g of the compound 17.

Melting point: 194.9–195.4° C.; Elemental analysis ($C_{24}H_{27}N_3O_3$): Calcd. (%): C, 71.09; H, 6.71; N, 10.36; Found (%): C, 71.26; H, 6.70; N, 10.44; IR (KBr) $cm^{-1}$: 1606, 1510, 1460, 1427, 1304, 1238, 1200, 1113, 1072; $^1$H-NMR δ (CDCl$_3$) ppm: 1.01 (3H, t, J=7.3 Hz), 1.68 (2H, t, J=7.3 Hz), 1.72 (6H, s), 2.43 (3H, s), 2.88 (2H, t, J=7.3 Hz), 3.55 (3H, s), 3.65 (3H, s), 5.84 (1H, s), 7.01 (1H, m), 7.19 (2H, s).

Examples 30–37

The recording membrane was formed in a manner completely similar to that in Example 12 except that the compound 10, 11, 12, 13, 14, 15, 16 or 17 was used instead of the compound 1 (Examples 30–37). The obtained optical constants of the resulting membrane are shown in the above Table 5. Furthermore, the recording medium was formed in a manner completely similar to that in Example 12 and the signal properties thereof were measured. The resulting signal properties are shown in the above Table 6.

Industrial Applicability

According to the present invention, there can be provided squarylium compounds having spectroscopic and thermal decomposition properties suitable for an oscillation wavelength of a semiconductor laser used for a digital versatile disc-recordable (DVD-R). Also, DVD-R media having the excellent light resistance as well as the high reflectance and modulation depth can be provided by using the squarylium compound of the present invention as a recording material.

What is claimed is:

1. A squarylium compound represented by the general formula (I):

(I)

wherein, $R^1$ represents a hydrogen atom, an alkyl group optionally having a substituent, an aryl group optionally having a substituent or a heterocyclic group optionally having a substituent; $R^2$ represents a hydrogen atom, a halogen atom, an alkyl group optionally having a substituent, an alkoxy group optionally having a substituent, an aralkyl group optionally having a substituent, an aryl group optionally having a substituent, an amino group optionally having a substituent or a heterocyclic group optionally having a substituent; $R^3$ and $R^4$ are the same or different, and represent an alkyl group, or $R^3$ and $R^4$ may be taken together with an adjacent carbon atom to form an alicyclic hydrocarbon ring or a heterocycle; $R^5$ represents a hydrogen atom, an alkyl group optionally having a substituent, an aralkyl group optionally having a substituent or an aryl group optionally having a substituent; $R^6$ represents a halogen atom, an alkyl group optionally having a substituent, an aralkyl group, an aryl group, a nitro group, a cyano group or an alkoxy group; and n represents an integer of 0–4, and when n is 2–4, then $R^6$s are the same or different, or two adjacent $R^6$s may be taken together with two adjacent carbon atoms to form an aromatic ring optionally having a substituent.

2. An optical recording medium, which comprises a recording layer containing the squarylium compound represented by the general formula (I) according to claim 1.

3. The optical recording medium according to claim 2, wherein the recording layer contains a light stabilizer.

4. The optical recording medium according to claim 3, wherein the light stabilizer is selected from the group consisting of a metal complex and an aromatic amine.

5. The optical recording medium according to claim 4, which contains 5–40% by weight of the light stabilizer relative to the squarylium compound.

6. The optical recording medium according to any one of claims 2–5, wherein a single layer of the recording layer has the refractive index (n) of 1.5≦n≦3.0 and the extinction coefficient (k) of 0.02≦k≦0.3 for the light of a wavelength range of a recording or reproducing wavelength ±5 nm.

7. The optical recording medium according to claim 2, wherein the squarylium compound has a temperature slope of the loss in weight in a principal loss-in-weight process in the thermogravimetric analysis of 1%/° C. or greater.

8. The optical recording medium according to claim 2, wherein the squarylium compound has a ratio of the loss in weight in the principal loss-in-weight process in the thermogravimetric analysis of 20% or greater and a weight losing-initiation temperature of 350° C. or lower.

9. The optical recording medium according to claim 2, which has a track pitch on a substrate within the range of 0.7–0.8 μm and a groove width at the half band width within the range of 0.20–0.36 μm.

10. The optical recording medium according to claim 2, which has a recording or reproducing wavelength within the range of 600–700 nm.

11. The optical recording medium according to claim 2, which has a maximum absorbing wavelength within the range of 550–600 nm and a log ε (ε is a molar extinction coefficient) at said maximum absorbing wavelength of 5 or bigger.

* * * * *